(12) United States Patent
Arnal et al.

(10) Patent No.: US 7,273,448 B2
(45) Date of Patent: Sep. 25, 2007

(54) MALE URETHRAL PROSTHESIS

(75) Inventors: Kevin R. Arnal, Excelsior, MN (US); Steven W. Siegel, North Oaks, MN (US)

(73) Assignee: AMS Research Corporation, Minnetonka, MN (US)

(*) Notice: Subject to any disclaimer, the term of this patent is extended or adjusted under 35 U.S.C. 154(b) by 136 days.

(21) Appl. No.: 10/924,274

(22) Filed: Aug. 23, 2004

(65) Prior Publication Data

US 2005/0055104 A1    Mar. 10, 2005

Related U.S. Application Data

(63) Continuation-in-part of application No. 10/422,630, filed on Apr. 24, 2003, now abandoned.

(51) Int. Cl.
*A61F 2/00* (2006.01)

(52) U.S. Cl. .................................................. 600/30

(58) Field of Classification Search ............ 600/29–31; 128/885, 912, DIG. 25
See application file for complete search history.

(56) References Cited

U.S. PATENT DOCUMENTS

| | | | |
|---|---|---|---|
| 3,789,828 | A | 2/1974 | Schulte |
| 4,019,499 | A | 4/1977 | Fitzgerald |
| 4,386,601 | A | 6/1983 | Trick |
| 4,552,128 | A | 11/1985 | Haber |
| 4,587,954 | A | 5/1986 | Haber |
| 4,682,583 | A | 7/1987 | Burton et al. |
| 4,878,889 | A | 11/1989 | Polyak |
| 4,994,020 | A | 2/1991 | Polyak |
| 5,163,897 | A | 11/1992 | Persky |
| 5,520,606 | A | 5/1996 | Schoolman et al. |
| 5,976,068 | A * | 11/1999 | Hakky et al. .............. 600/29 |
| 6,095,969 | A * | 8/2000 | Karram et al. .............. 600/31 |
| 6,117,067 | A | 9/2000 | Gil-Vernet |
| 6,171,230 | B1 * | 1/2001 | Hakky et al. .............. 600/29 |
| 6,258,098 | B1 | 7/2001 | Taylor et al. |
| 6,382,214 | B1 | 5/2002 | Raz et al. |
| 6,502,578 | B2 | 1/2003 | Rax et al. |

(Continued)

FOREIGN PATENT DOCUMENTS

DE    195 11 998    10/1996

(Continued)

OTHER PUBLICATIONS

Daher, N. et al., "Pre-pubic TVT: An alternative to classic TVT in selected patients with urinary stress incontinence," *European Journal of Obstetrics & Gynecology & Reproductive Biology*, vol. 167, p. 205-207 (2003).

(Continued)

*Primary Examiner*—John P. Lacyk
(74) *Attorney, Agent, or Firm*—Jose W. Jimenez

(57) ABSTRACT

The present invention provides a urethral prosthesis including a substrate, an inflatable pillow attached to the substrate, a pressurized reservoir in fluid communication with the pillow and a restrictor. Upon compression of the inflatable pillow, inflating agent is transferred from the inflatable pillow to the pressurized reservoir. Upon terminating compression, inflating agent returns to the inflatable pillow. The urethral prosthesis may be implanted such that the inflatable pillow prevents unintentional voiding of a patient's bladder.

30 Claims, 6 Drawing Sheets

U.S. PATENT DOCUMENTS

| | | |
|---|---|---|
| 6,506,190 B1 | 1/2003 | Walshe |
| 6,579,225 B2 | 6/2003 | Pregenzer et al. |
| 6,612,977 B2 | 9/2003 | Staskin et al. |
| 6,652,450 B2 | 11/2003 | Neisz et al. |
| 6,755,781 B2 | 6/2004 | Gellman |
| 6,802,807 B2 | 10/2004 | Anderson et al. |
| 2001/0023356 A1 | 9/2001 | Raz et al. |
| 2002/0128670 A1 | 9/2002 | Ulmsten et al. |
| 2002/0147382 A1 | 10/2002 | Neisz et al. |
| 2002/0156487 A1 | 10/2002 | Gellman et al. |
| 2002/0161382 A1 | 10/2002 | Neisz et al. |
| 2003/0065402 A1 | 4/2003 | Anderson et al. |
| 2003/0130670 A1 | 7/2003 | Anderson et al. |

FOREIGN PATENT DOCUMENTS

| | | |
|---|---|---|
| EP | 0 409 592 | 1/1991 |
| EP | 0 650 703 | 6/1994 |
| WO | WO 00/18319 | 4/2000 |
| WO | WO 00/74633 | 12/2000 |
| WO | WO 01/45588 | 6/2001 |
| WO | WO 2004/016196 | 2/2004 |

OTHER PUBLICATIONS

Dargent, D., et al. Pose d'un ruban sous uretal oblique par voie obturatrice dans le traitement de l'incontinence urinaire feminine. Gynecol Obstet Fertil 2002: 30: (2002) (Provided in both French and English languages).

Comiter. C., "The male sling for stress urinary incontinence: A Prospective Study," *Journal of Urology*, vol. 167, No. 2, Part 1 of 2, p. 597-600 (Feb. 2002).

Mulcahy, *Tips for successful placement of the artificial urinary sphincter*, Contemporary Urology, Sep. 1995, pp. 1-5.

Petrou, et al., *Artificial Urethral Sphincter for Incontinence*, UROLOGY 56: 353-359, 2000.

Product Sheet, "In Vance Male Sling System," American Medical Systems, Inc. (2001).

"Urinary Incontinence: Easier Operation", Article from La Libre Belgique. Wednesday, Oct. 15, 2003 (English Translation).

\* cited by examiner

MALE URETHRAL PROSTHESIS

CROSS-REFERENCE TO RELATED APPLICATIONS

This application is a continuation-in-part of U.S. patent application Ser. No. 10/422,630 filed Apr. 24, 2003, now abandoned entitled "Male Urethral Prosthesis," and which is hereby incorporated by reference.

BACKGROUND OF THE INVENTION

Urinary incontinence is a condition characterized by involuntary loss of urine beyond the individual's control. One cause for this loss of control is damage to the urethral sphincter caused by, for example, prostatectomy, radiation therapy or pelvic accidents. Other causes of incontinence include bladder instability, over-flowing incontinence and fistulas.

Currently, there are a few known surgical treatments for male incontinence, including the implantation of an Artificial Urinary Sphincter (e.g. AMS Sphincter 800 available from American Medical Systems, Minnetonka, Minn.), the implantation of a bone-screw fixated male sling (e.g. AMS InVance, available from American Medical Systems), and a few other procedures. Other procedures that have been largely discontinued include the implantation of a kaufman III Prosthesis beneath the urethra. All of these prostheses exert a force on the urethra to prevent unintentional voiding of the bladder.

An improved urethral prosthesis has also been reported, in which a fluid filled chamber is incorporated into the prosthesis to provide improved treatment of incontinence. For example, U.S. Pat. No. 6,502,578 and U.S. Publish Patent Application 2001/0023356, both to Raz et al. report an apparatus and method for treatment of male incontinence in which a "hammock-like" prosthesis is positioned between the descending rami of the pubic bone. The prosthesis includes an inflatable balloon device positioned to provide passive compression on the bulbar urethra to prevent voiding of the bladder. The volume of the balloon may be adjusted after implantation in a patient with a needle and syringe device.

PCT Published Application No. WO 00/74633 A2 reports a urethral prosthesis including a tape having an expandable pillow adapted to be positioned between the tape and the urethra after implantation. The pillow may be expanded by injecting bulking agent into the pillow, resulting in a vertical lifting against the urethra.

U.S. Pat. No. 3,789,828 to Schulte reports a urethral prosthesis including a capsule having a liquid filled cavity and two flexible prosthesis ties. U.S. Pat. No. 4,019,499 to Fitzgerald reports a compression implant for urinary incontinence including a cap with an external planar pressure face, a base with an external bearing face and a wall connecting the cap and the base. The cap, base and wall form a cavity that may be filled with an adjustable amount of fluid to adjust the force exerted against the urethra after implantation.

U.S. Pat. No. 6,117,067 to Gil-Vernet reports a device for adjusting the height of internal anatomical organs. The device includes a chamber with a volume that may be adjusted by varying the amount of fluid in the chamber. A capsule connected to the chamber via a tube may be used to increase or decrease the amount of fluid in the chamber. Each end of a thread is connected to an end of the chamber, and the thread is adapted to surround an organ. By adjusting the volume of the chamber the thread lifts or lowers the organ as desired.

PCT Application 00/18319 reports a prosthesis including a flexible elongate member, a distensible portion, a conduit and a valve. The distensible portion is bonded to the elongate member and may be filled with a fluid. The conduit provides fluid communication between the distensible portion and the valve. Fluid may be injected into the valve to adjust the pressure of the distensible portion.

Although urethral prostheses that incorporate adjustable fluid-filled chambers may reduce unintentional voiding of the bladder, current chambers may suffer from one or more drawbacks. For example, if the chambers are not sufficiently inflated before implantation, a clinician must inject additional fluid into the chamber to place sufficient force against the patient's urethra. However, this fluid puts additional strain on the prosthesis material, which is generally anchored to an anatomical structure in the body. Such strain may cause patient discomfort, or may even cause the prosthesis to fail. In another example, if the chamber exerts too much pressure on a patient's urethra, then the patient may be unable to void the bladder. This too would require a clinician to perform an additional procedure to adjust the fluid level in the chamber, which would subject the patient to additional risk of infection and may make the procedure more costly. Further yet, such devices have little tolerance for improvement or deterioration in the patient's incontinence condition. Thus, it would be advantageous to provide a male urethral prosthesis that overcomes one or more of these drawbacks.

SUMMARY OF THE INVENTION

The present invention provides a urethral prosthesis including a biocompatible implantable substrate, an inflatable pillow attached to the substrate that is adapted to house an inflating agent, a pressurized reservoir in fluid communication with the inflatable pillow and a restrictor to regulate transfer of the inflating agent between the pressurized reservoir and the inflatable pillow. Upon compression of the inflatable pillow, the inflating agent is adapted to transfer from the pillow to the pressurized reservoir. However, upon terminating compression of the inflatable pillow, the inflating agent is adapted to transfer from the pressurized reservoir to the pillow. The prosthesis may further include a conduit to facilitate transfer of the inflating agent between the inflatable pillow and the pressurized reservoir. As used herein, the phrase "inflatable pillow" refers to a reservoir or other structure that is capable of holding or housing a sufficient amount of fluid to exert a pressure on a patient's urethra.

In another embodiment, the present invention provides a urethral prosthesis including an implantable substrate, an inflatable pillow attached to the substrate that has an inflated mode and a deflated mode, and a pressurized reservoir in fluid communication with the inflatable pillow that is adapted to house a portion of the inflating agent. Upon compression of the inflatable pillow when in the inflated mode, the inflatable pillow adjusts to the deflated mode. However, upon terminating compression of the inflatable pillow, the inflatable pillow returns to the inflated mode after a sufficient period of time to allow voiding of a patient's bladder.

In yet another embodiment, the present invention provides a method for treating urinary incontinence in which an embodiment of the urethral prosthesis described above is implanted in a patient. An inflatable pillow attached to a substrate is implantably secured in the patient such that the inflatable pillow is positioned to exert a force on a portion of the patient's urethra when in an inflated mode. After implantation, a pressure may be exerted on the inflatable pillow to deflate the pillow to reduce the force exerted on the portion of the patient's urethra. The pressure exerted on the inflatable pillow is then reduced to allow the inflatable pillow to inflate. Before the inflatable pillow returns to the inflated mode, a patient's bladder may be voided without resistance against the urethra from the inflatable pillow. However, the inflatable pillow may adjust to the inflated mode prior to a subsequent, unintentional voiding of a patient's bladder.

In a further embodiment, the present invention provides a method of treating urinary incontinence, in which a urethral prosthesis is implanted into a patient. The prosthesis includes an implantable substrate that may be secured to the patient's body tissue, an inflatable pillow that is attached to the substrate and exerts a force on a portion of the patient's urethra, and a detachable fluid adjustment port in fluid communication with the pillow.

After implanting the prosthesis, the patient's condition may be monitored by a clinician. If desired and/or necessary, fluid may be added to or removed from the pillow via the fluid adjustment port. Alternatively or additionally, the clinician may detach the fluid adjustment port and attach a pressurized fluid system that includes a pressurized reservoir in fluid communication with the pillow, and a restrictor that regulates the transfer of fluid between the pressurized reservoir and the pillow.

DETAILED DESCRIPTION

Figure 1:
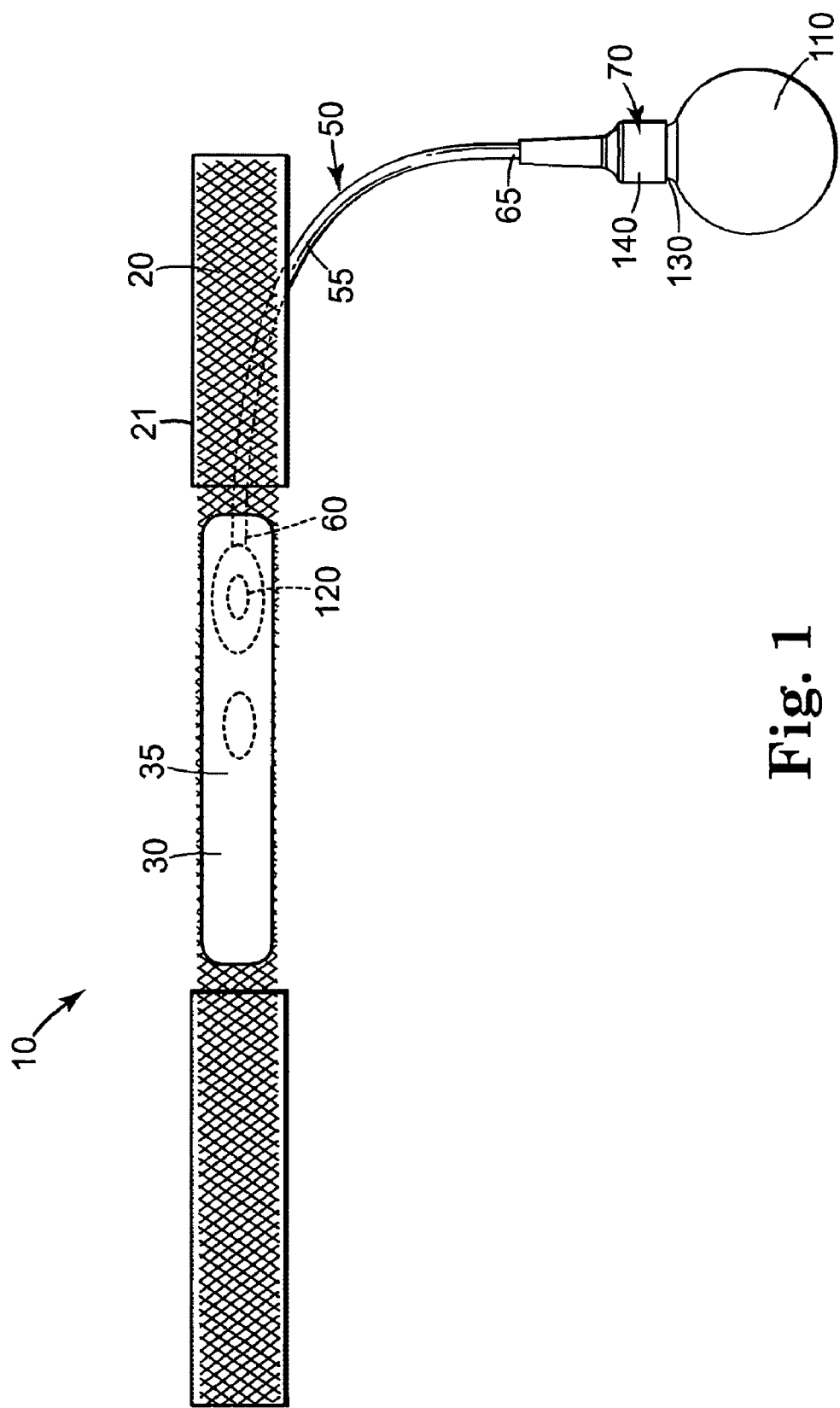
FIG. 1 schematically illustrates a top view of an embodiment of the present invention.
Figure 2:
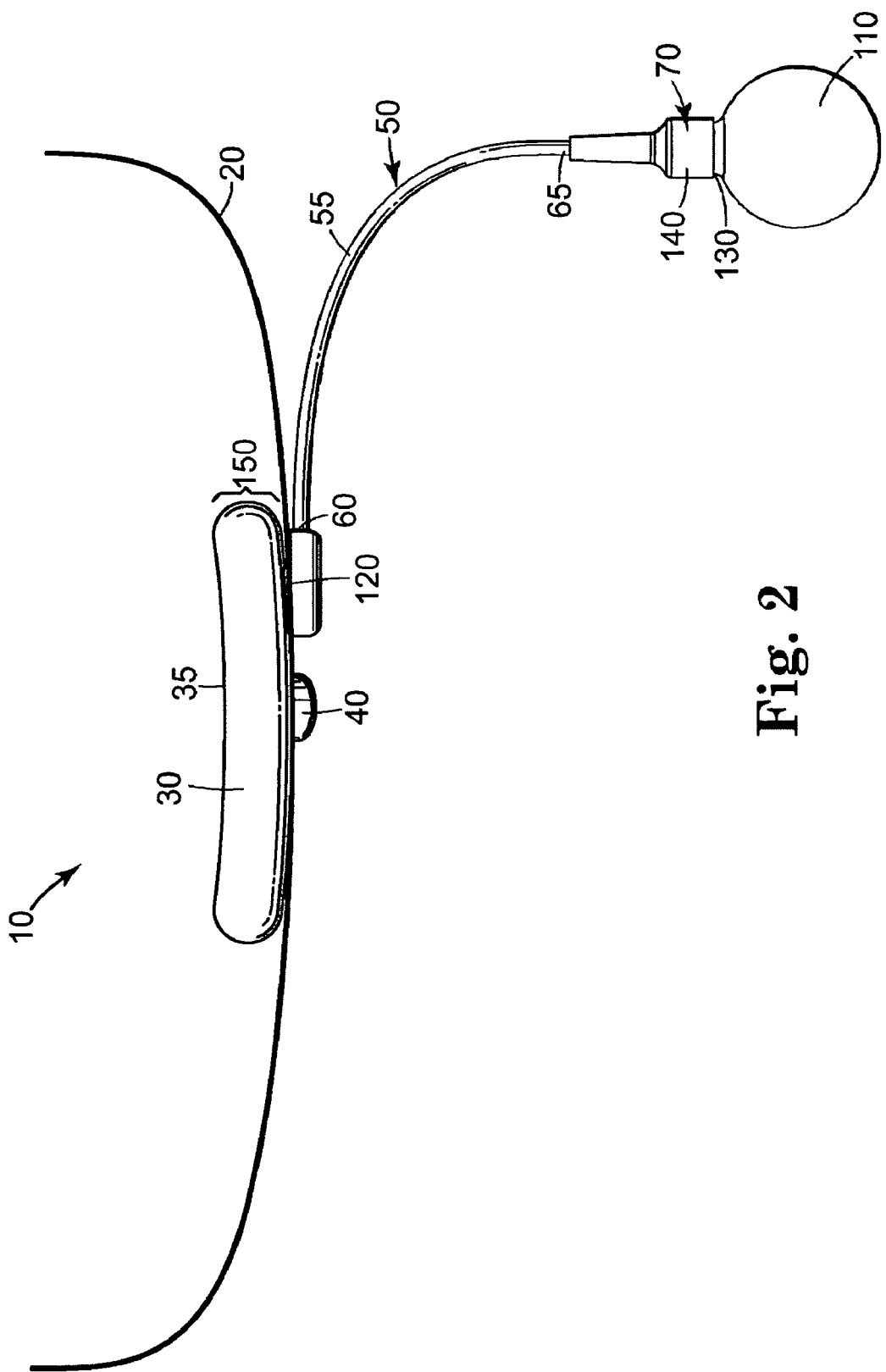
FIG. 2 schematically illustrates a side view of an embodiment of the present invention in an inflated mode.
Figure 3:
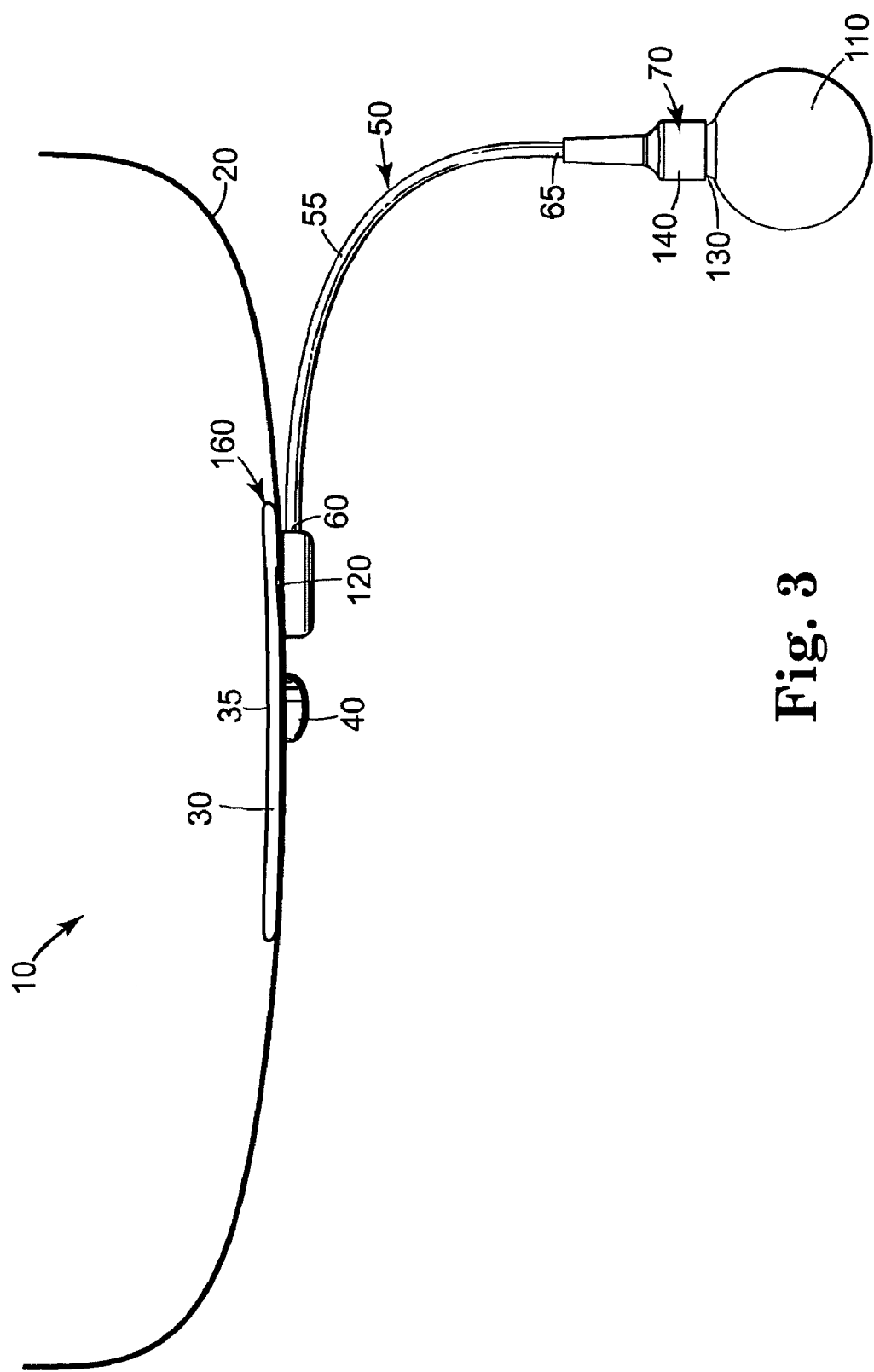
FIG. 3 schematically illustrates a side view of the embodiment of FIG. 2 in a deflated mode.

As illustrated in FIGS. 1-3, one embodiment of the urethral prosthesis 10 of the present invention includes a substrate 20, an inflatable pillow 30, a conduit 50, a restrictor 70 and a pressurized reservoir 110.

The substrate 20 in this embodiment may be a length of flexible, longitudinally extendable material. The material may be inelastic or elastic, longitudinally extendable or non-extendable and may be patterned, for example in a mesh pattern, which may encourage tissue in-growth. Suitable materials for the substrate may include, but are not limited to materials such as polyester, polypropylene, nylon, polyethylene terephthalate, polytetrafluorethylene, expanded polytetrafluoroethylene (e.g. Gortex), polyvinylidene fluoride, polyamides and silk. Preferably, at least the end portions of the substrate 20 may be configured, for example configured as a mesh, to promote tissue in-growth. Alternatively, the substrate 20 may be at least partially formed from a bioabsorbable material such as polylactic acid or polyglycolic acid. Suitable materials are also reported in U.S. Published Patent Application No. 2002/0147382. Still further, the substrate 20 may be coated with a suitable bioactive material having a desired physiological effect. For example, suitable bioactive materials may be selectively coated on desired areas or portions of the urethral prosthesis 10 to reduce inflammation, encourage tissue in-growth and/or to prevent infection in specific areas of a patient.

In one embodiment, the substrate 20 is a polymeric mesh coated with a silicone material or other suitable material, such as an elastomer, polyethylene, polypropylene, polyester or polyurethane, or a derivative or combination thereof. In another embodiment, an insertion sheath 21 may be optionally used. For example, insertion sheath 21 may be used when the substrate 20 is formed from a longitudinally extending mesh. Suitable materials for the sheath 21 include polyethylene, polypropylene, nylon, polyester, and polytetrafluoroethylene. Other suitable sheaths are reported in co-pending U.S. patent application Ser. No. 10/335,119, filed Dec. 31, 2002.

Optionally, the substrate 20 may also include a tensioning member, such as a tensioning suture or filament. Suitable tensioning members are disclosed in U.S. Published Patent Application Nos. 2002/0107430-A1 and 2003/0065402 A1, and U.S. patent application Ser. No. 10/335,119. Additionally, the substrate 20 may include suitable connectors or dilators to facilitate implantation in a patient with guide instruments as reported in further detail below.

The substrate 20 may be sized and shaped for implantation and attachment in the vicinity of a patient's descending rami. In one embodiment, the substrate 20 may have a length between about 5 and about 25 cm, more particularly between about 10 and about 15 cm. The substrate 20 may have a width of between about 0.5 and about 5 cm, more particularly between about 1.5 and about 2.5 cm. The width along the substrate 20 may vary The inflatable pillow 30 may be attached to the substrate 20 in any suitable manner. For example, inflatable pillow 30 may be attached by a suitable adhesive. Alternatively, the urethral prosthesis 10 may have an intermediate layer (not shown) to facilitate attachment between the substrate 20 and the inflatable pillow 30.

The inflatable pillow 30 may be attached approximately at a center point of the substrate 20. A variety of shapes may be used for the inflatable pillow 30. In the illustrated embodiment, the inflatable pillow 30 is a generally oblong shape having rounded edges. From the side perspective of FIG. 2, inflatable pillow 30 possesses a concave upper face 35, however, other embodiments may possess a comparatively flat or convex upper face 35 to provide maximum surface area for contact with a urethra of a patient. The size of inflatable pillow 30 may vary widely, however, in one embodiment, the inflatable pillow 30 has a major dimension between about 1 and about 10 cm and a minor dimension between about 0.5 and about 3 cm. In another embodiment, the inflatable pillow 30 may be positioned transverse with respect to the length of the substrate 20.

The inflatable pillow 30 may be formed from any suitable material capable of withstanding a sufficient volume of pressurized fluid to prevent unintentional voiding of a patient's bladder. Suitable materials may include, but are not limited to include elastomers, silicones, polypropylenes, polyesters, polyurethanes, polyvinyl chlorides and polyamides. The inflatable pillow 30 also generally includes an opening 120 to facilitate the delivery and receipt of inflating agent from the pressurized reservoir 110.

The pressurized reservoir 110 is in fluid communication with the inflatable pillow 30 and is capable of pressurizing varying amounts of inflating agent such that the entire fluid system (i.e., the reservoir, inflatable pillow, conduit and restrictor) is pressurized. The pressurized reservoir 110 may be an expandable material having a generally spherical shape. The pressurized reservoir 110 may be formed from any suitable material capable of delivering and receiving inflating agent. Suitable materials may include, but are not limited to elastomers, silicones, polypropylenes, polyesters and polyurethanes. The pressurized reservoir 110 also includes an opening 130 to facilitate the receipt and delivery of inflating agent. The pressurized reservoir 110 may be sized and shaped for implantation in the scrotum of a patient.

The inflatable pillow 30 and the pressurized reservoir 110 fluidly communicate via conduit 50. Conduit 50 includes a tube 55 having a first end 60 and a second end 65. The first end 60 communicates with opening 120 of the inflatable pillow 30. The tube 55 may be formed from a flexible polymeric material that is resistant to kinks. Suitable materials for the tube 55 may include, but are not limited to, flexible polymeric materials such as elastomers, silicones, polypropylenes, polyesters, polyurethanes and polyvinyl chlorides. The tube 55 may be reinforced with a variety of suitable materials to impart additional kink resistant properties.

Restrictor 70 is attached to tube 55 at an opening 135, and is attached to reservoir 110 at an opening 131. The restrictor 70 is adapted to regulate the flow of inflating agent between the inflatable pillow 30 and the pressurized reservoir 110. More particularly, the restrictor 70 allows inflating agent to flow from the inflatable pillow 30 to the pressurized reservoir 110 during compression of the inflatable pillow, but resists flow of inflating agent from the pressurized reservoir 110 to the inflatable pillow 30.

Figure 4:
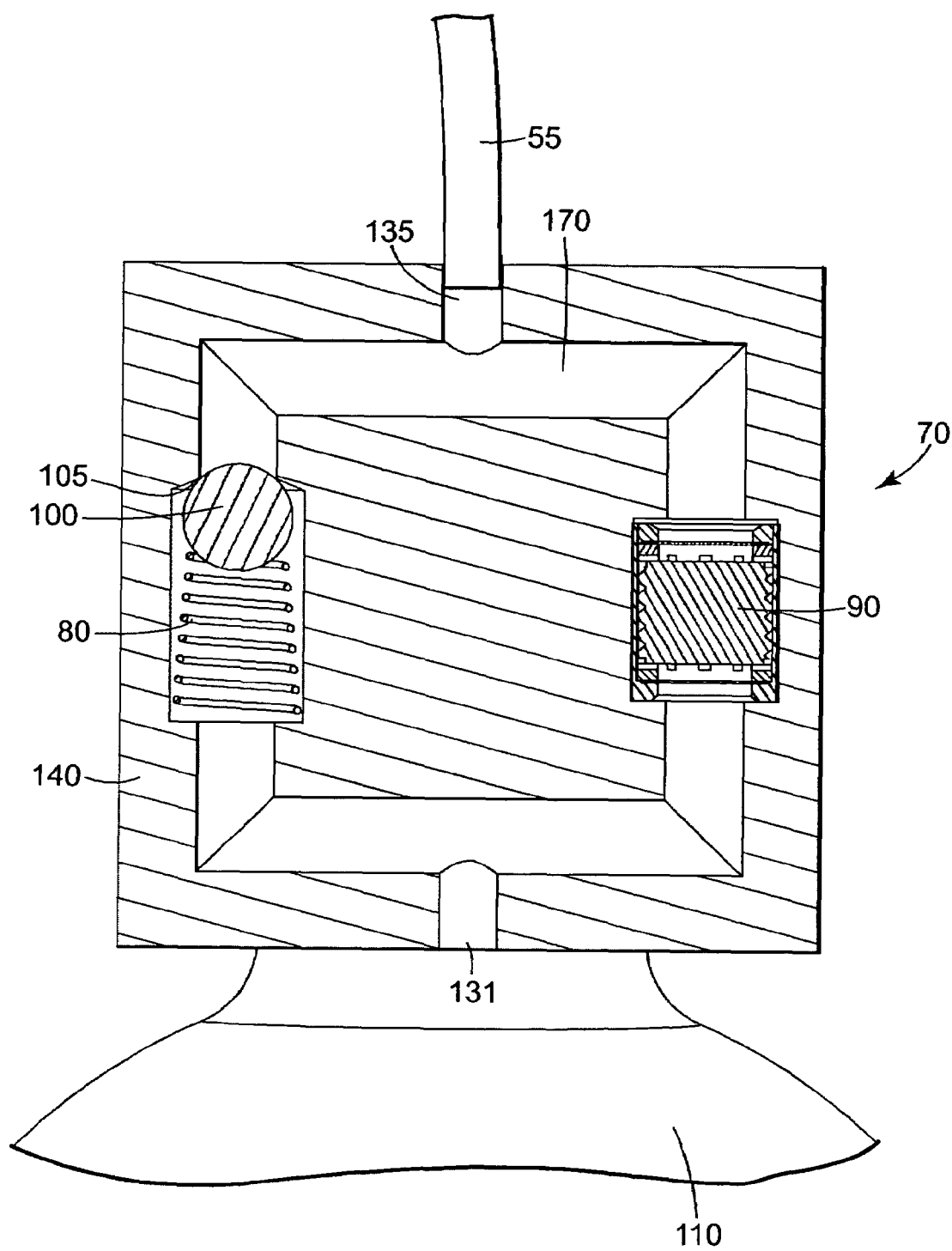
FIG. 4 schematically illustrates a partial cross-section of a restrictor portion suitable for use with an embodiment of the present invention.

As illustrated in FIG. 4, restrictor 70 may include a housing 140, a channel 170, a spring 80, a fluid resistor 90, a ball 100 and a valve seat 105. The fluid resistor provides a narrow channel or orifice through which inflating agent may travel. The ball 100, spring 80 and valve seat 105 cooperate to allow inflating agent to travel from the inflatable pillow 30 to the pressurized reservoir 110, but to prevent the inflating agent from traveling in the reverse direction except through the fluid resistor 90.

In an alternative embodiment, the fluid resistor 90 may include a valve or other means to provide regulated flow from the pressurized reservoir 110 to the inflatable pillow 30. For example, the fluid resistor 90 may be combined with the ball 100, and spring 80 such that the inflating agent only travels along a single path while in the restrictor 70. More particularly, the valve seat 105 for the ball 100 could have small holes to duplicate the action of the resistor 90 and thus eliminate the separate fluid resistor 90 from the restrictor 70.

In the illustrated embodiment, the restrictor 70 is adjacent to the pressurized reservoir 110. Other configurations are possible that place the restrictor at different proximities to the pressurized reservoir 100 and the inflatable pillow 30. In one embodiment, for example, the restrictor may be positioned between the inflatable pillow 30 and the pressurized reservoir 110 with conduits attached to openings 131 and 135 to provide fluid communication. In another embodiment, the restrictor housing 140 may be positioned adjacent to the inflatable pillow 30 with the opening 135 of the restrictor 70 communicating with the opening 120 of the inflatable pillow 30. In this embodiment, the opening 131 of the restrictor 70 would fluidly communicate with the opening 130 of the pressurized reservoir 110 via conduit 50.

In one embodiment, the urethral prosthesis may also include an optional compression region 40. The compression region 40 provides a tactile locator for operating the prosthesis as described below. The compression region 40 may be attached to, or in communication with the inflatable pillow 30, and may be located on a lower face of the inflatable pillow 30. Alternatively, the compression region may be attached to a portion of the substrate 20 upon which the inflatable pillow 30 is attached.

The inflating agent used in the urethral prosthesis 10 may be any material consistent with the function of the present invention. Suitable inflating agents are generally fluids, such as gasses or aqueous solutions. The viscosity of the fluid may range from 0.2 centipoise to 1000 centipoise.

In operation, the inflatable pillow 30 is adapted to adjust between an inflated mode 150 shown in FIG. 2 and a deflated mode 160, exemplified in FIG. 3. When fluid is transferred to the reservoir 110 from the inflatable pillow 30, the pressure within the pressurized reservoir 110 forces fluid back to the pillow 30 through the restrictor 70. This process continues until the pillow 30 and reservoir 110 have reached fluid equilibrium. The amount of fluid transferred to the pillow 30 is dependent on the amount of fluid required for the reservoir 110 and pillow 30 to reach equilibrium.

When the internal pressure between the pressurized reservoir 110 and the inflatable pillow 30 is at equilibrium, sufficient amounts of the inflating agent are present in the inflatable pillow 30 such that the inflatable pillow 30 is in the inflated mode 150. In the inflated mode 150, the inflatable pillow 30 may have an internal "physiological" pressure sufficient to prevent unintentional voiding of a patient's bladder, without causing necrosis of the urethra. In one embodiment the pressure of the inflatable pillow may be between about 50 and about 300 cm $H_2O$, more particularly, between about 50 and about 140 cm $H_2O$, even more particularly, between about 50 and about 70 cm $H_2O$.

When a sufficient force is exerted on the inflatable pillow 30 when in the inflated mode 150, inflating agent transfers from the inflatable pillow 30, through the conduit 50 and restrictor 70 and into the pressurized reservoir 110 . In this embodiment, the inflatable pillow 30 may be compressed from an inflated mode 150 as shown in FIG. 2 to a deflated mode 160 as shown in FIG. 3. As used herein, the term "deflated mode" refers to the inflatable pillow after sufficient compression is exerted on the inflatable pillow to transfer inflating agent to the reservoir 110 and to allow voiding of a patient's bladder. As is evident from the foregoing, even in the deflated mode, the inflatable pillow 30 may house a volume of inflating agent.

When the compression is reduced or terminated, the inflating agent transfers from the pressurized reservoir 110 to the inflatable pillow 30. The transfer of the inflating fluid to the inflatable pillow 30 may be regulated by several factors. First, the pressurized reservoir 110 is adapted to exert sufficient pressure on the inflating fluid such that inflating agent transfers to the inflatable pillow 30 without requiring a pump system. However, the restrictor 70 regulates the rate of transfer of the inflating agent between the pressurized reservoir 110 and the inflatable pillow 30. More particularly, upon reducing or terminating compression on the inflatable pillow 30, the restrictor 70 resists transfer of inflating fluid from the pressurized reservoir 110 to the inflatable pillow 30, such that the inflatable pillow 30 does not adjust to the inflated mode 150 instantaneously, but rather, inflation occurs over a sufficient period of time to allow a patient's bladder to be voided. For example, after terminating compression of the inflatable pillow 30, the inflatable pillow 30 may return to the inflated mode 150 over a period of between about 30 seconds and about 7 minutes, more particularly between about 1 and about 4 minutes, even more particularly between about 2 and about 3 minutes.

Figure 5:
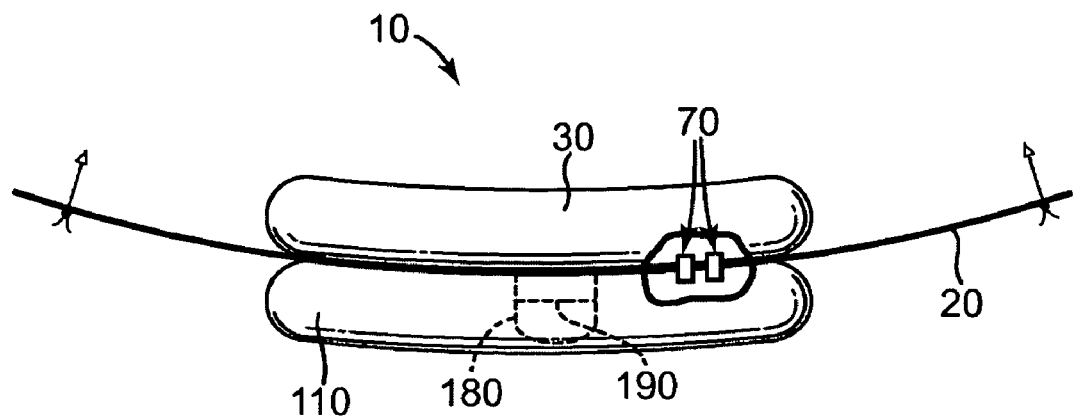
FIG. 5 schematically illustrates a side view of an embodiment of the present invention in an inflated mode.

In an alternate embodiment illustrated in FIG. 5, the urethral prosthesis 10 of the present invention does not include a conduit 50. Instead, the pressurized reservoir 10 is attached onto the side of the substrate 20 opposite the inflatable pillow 30. The restrictor 70 provides fluid communication between the pressurized reservoir 110 and the inflatable pillow 30. The restrictor 70 may include a fluid resistor 90 and a check valve 195 the same as or similar to the resistor illustrated in FIG. 4. The pressurized reservoir 110 may further include a stiffener 180 that acts as the optional compression region 40 reported above. The stiffener 180 may be formed from silicone, and may include a fluid orifice 190 that is in fluid communication with the pressurized reservoir 110. In operation, the prosthesis transfers fluid between the pressurized reservoir 110 and the inflatable pillow 30 in the same manner as the embodiments illustrated in FIGS. 1-3.

Figure 6:
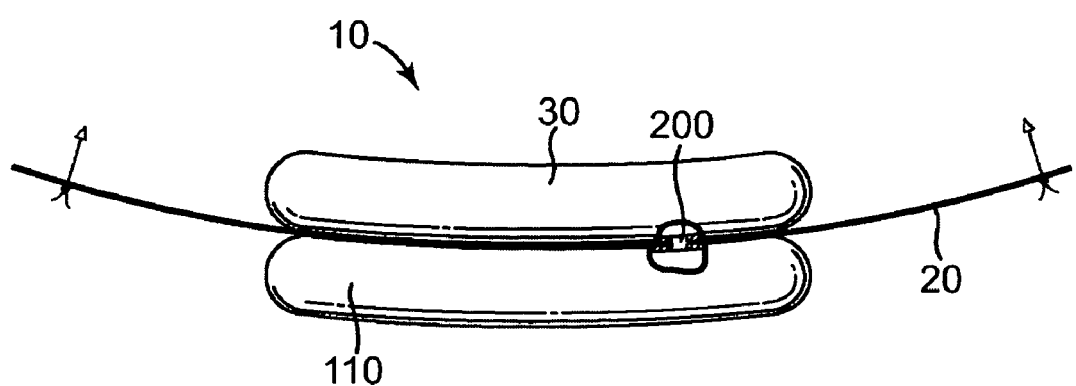
FIG. 6 schematically illustrates a side view of an embodiment of the present invention in an inflated mode.

The urethral prosthesis 10 illustrated in FIG. 6 is similar to the embodiment shown in FIG. 5, except that the prosthesis 10 does not include a stiffener 180, and the restrictor 70 includes a fluid orifice 200, rather than a resistor 90 or a valve as in previous embodiments.

Because of the different restrictor 70 configuration, the urethral prosthesis illustrated in FIG. 6 functions somewhat differently than the previously reported embodiments. Most significantly, the inflatable pillow 30 does not alternate between an inflated mode (FIG. 2) and a deflated mode (FIG. 3) Instead, the inflatable pillow 30 remains substantially permanently inflated. Although changes in various forces exerted against the inflatable pillow may cause fluid to transfer into or out of the pressurized reservoir via the fluid orifice 200, substantially continuous pressure is exerted against a patient's urethra by the inflatable pillow 30.

The urethral prosthesis 10 of the present invention may be implanted in a patient by a variety of suitable methods. Suitable implantation methods are reported, for example in U.S. Pat. No. 6,502,578 to Raz et al., incorporated herein by reference. In one embodiment, a small scrotal incision is made. The urethral prosthesis 10 is then positioned in the vicinity of a patient's descending rami of the pubic bone such that the inflatable pillow 30 exerts a sufficient force on a portion of a patient's urethra, particularly the bulbar urethra, to prevent unintentional voiding of the bladder. The pressurized reservoir 110 may be implanted in the scrotum of a male patient.

In an alternate embodiment, a small transverse scrotal incision and one or two small horizontal suprapubic incisions are made. A suitable guide needle, similar to the needles reported in U.S. Published Patent Application Nos. 2002/0147382, 2002/0099259 A1, 2002/0099258 A1 and 2001/0161382 may be inserted into the first suprapubic incision and passed either anterior or superior to the pubic symphysis and towards the scrotal incision. Once a first guide needle has been successfully guided and/or positioned, a second guide needle may be inserted through the optional second suprapubic incision and positioned and/or guided in a similar manner, in opposition to the first needle. The distal ends of the guide needles may then be secured to the optional dilators or connectors attached to the ends of substrate 20, and the urethral prosthesis 10 may be pulled up through the suprapubic incisions. During the implantation procedure, the substrate may be at least partially covered with one or more heat sealed plastic sheaths (not shown), which are removed prior to completing the procedure.

The urethral prosthesis 10 may then be positioned in the vicinity of a patient's descending rami of the pubic bone such that the inflatable pillow 30 contacts a portion of the patient's urethra. The pressure exerted on the urethra may be adjusted during implantation. For example, the pressure may be increased by pulling on the ends of the substrate 20 until a sufficient force is exerted on the urethra. Alternatively, the pressure may be reduced by exerting downward tension in the vicinity of the inflatable pillow 30. The optional tensioning members may facilitate adjustments to the urethral prosthesis 10.

The urethral prosthesis 10 may be secured internally within the patient in a variety of suitable manners. In one embodiment, the urethral prosthesis 10 may be secured solely by tissue in-growth and/or tissue encapsulation. More specifically, portions of the substrate 20 may be configured, for example, in a mesh configuration, to encourage tissue in-growth. Other portions of the prosthesis 10, such as the inflatable pillow 30, may be configured in a manner that does not promote tissue in-growth, but may allow for tissue encapsulation. During the weeks and months after implantation, portions of the urethral prosthesis 10 may become increasingly secured within the patient by tissue in-growth and/or tissue encapsulation. In this manner, portions that are in-grown with tissue secure the urethral prosthesis 10, while portions that are encapsulated in tissue allow for some movement of portions of the urethral prosthesis 10 during use. Advantageously, this embodiment does not require (but may include) additional bone or soft tissue anchors to further secure the urethral prosthesis 10.

In an alternate embodiment, the substrate 20 may be secured to a soft tissue region, such as at the obturator internus muscles or the gracilis muscles, with a combination of suitable soft tissue anchors and sutures. In an additional embodiment, a combination of tissue in-grown portions and suitable anchors may secure the urethral prosthesis 10.

In yet another embodiment, the urethral prosthesis 10 may be secured to the pelvic origin of the gracilis tendon. For example, a tissue anchor may be implanted in the most proximal position to the inferior pubic ramus, where the gracilis tendon attaches to the bone. After the tissue anchor is inserted lateral to the tendon, a suture may be passed medial through the tendon to secure the prosthesis in place. This technique may be used on both sides of the body in opposition to secure the urethral prosthesis 10. A variety of suitable tissue anchor designs and materials may be used for securing the urethral prosthesis 10 in this embodiment. In one embodiment, for example, a "T" shaped tissue anchor may be formed from titanium, plastic, or stainless steel and may be deployed with a suitable deployment tool and attached to a suture to secure the sling to the tissue.

In an alternate embodiment, one or more tissue anchors may be used to secure the urethral prosthesis to the obturator internus muscles. The anchor may be deployed through the obturator foramen and pass through the obturator externus muscle to the obturator internus muscle. The anchor may then be positioned in the anterior recess of the ischio-anal fossa, just anterior to the obturator internus muscle. At least one anchor in each obturator internus muscle in opposition may be used to secure the sling in place. In a further embodiment, the urethral prosthesis 10 may be secured in this position by screwing a bone screw proximal to the gracilis tendon into the inferior pubic ramus. Alternatively, the urethral prosthesis may be secured to the superior or inferior pubic rami with a bone screw.

Once the embodiments illustrated in FIGS. 1-3 and 4 are implanted, the inflatable pillow 30 may be deflated by exerting tactile pressure on the patient's skin at a region that is in the vicinity of the inflatable pillow 30, more particularly, the optional compression region 40. The inflatable pillow 30 then deflates, reducing the force on a portion of the patient's urethra to allow the patient's bladder to be intentionally voided. After reducing or terminating pressure on the inflatable pillow 30 (normally prior to voiding) the inflatable pillow 30 returns to the inflated mode 150 over a period of time sufficient to allow voiding of the patient's bladder without allowing a subsequent unintentional voiding of the bladder.

In embodiments in which the urethral prosthesis 10 is secured at least partially by tissue in-growth, it may be desirable to maintain the inflatable pillow 30 in a deflated mode until sufficient tissue in-growth has occurred, and then "activating" the urethral prosthesis such that the inflatable pillow 30 is in the inflated mode 150 absent compression. This activation feature may be accomplished by several methods. For example, the urethral prosthesis may be implanted without the pressurized reservoir 110 being pressurized with inflating agent by, for example, injecting inflating agent into the pressurized reservoir 110. After sufficient tissue in-growth has occurred, the pressurized reservoir 110 may then be pressurized with inflating agent. Alternately, the urethral prosthesis may include a lock-out valve (not shown) that prevents inflating agent from filling the inflatable pillow 30. After sufficient tissue in-growth has occurred, the lock-out valve may be released to allow the inflatable pillow to expand to the inflated mode 150 to place additional pressure on a portion of a patient's urethra.

Advantageously, after initial implantation, the patient may perform the method reported herein without the assistance of a clinician. Further, compression and inflation of the inflatable pillow 30 places no additional stress on the substrate 20 because compressing the pillow actually reduces stress on the substrate. Thus, the urinary prosthesis 10 may be implanted in such a manner that voiding of a patient's bladder is not possible without deflating the inflatable pillow 30. Furthermore, the pillow allows a consistent pressure to be maintained on a portion of the urethra over time regardless of any changes that may occur in the space between the substrate 20 and the urethra. This may significantly reduce the adjustments required in conventional fluid filled devices to determine the precise pressure at which the patient's bladder may be intentionally voided while still preventing unintentional voiding.

Figure 7:
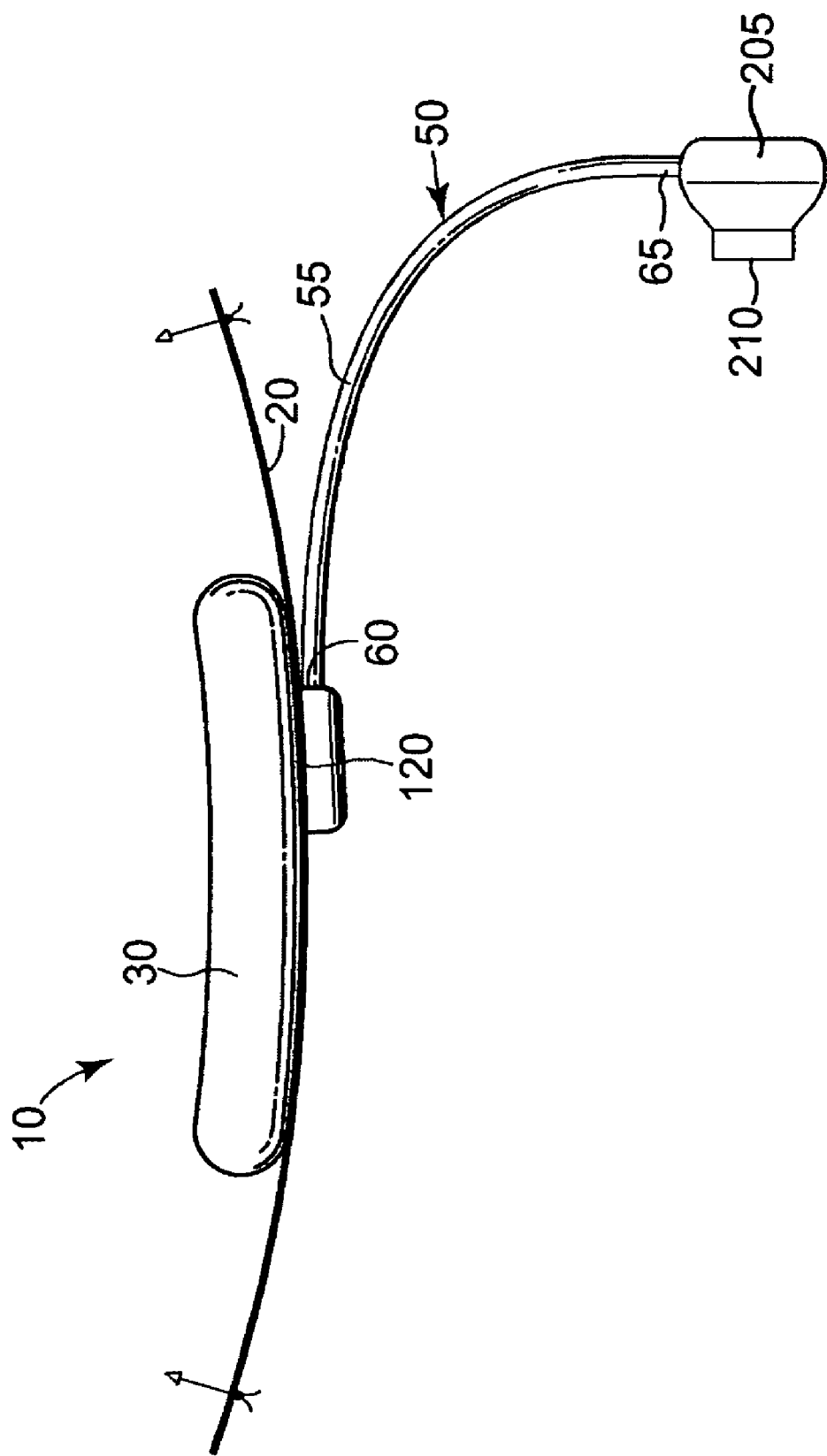
FIG. 7 schematically illustrates an alternate embodiment of the present invention.

Alternatively, the urethral prosthesis 10 illustrated in FIG. 7 may be initially implanted in the patient as reported above. This urethral prosthesis 10 includes many of the same features of the previously reported embodiments, except that this prosthesis includes a detachable fluid adjustment member 205 connected to the conduit 50 (or directly to the inflatable pillow 30) instead of the pressurized reservoir 110 and/or the restrictor 79 illustrated in previous embodiments. Fluid may be added to or removed from the inflatable pillow 30 through fluid adjustment port 210 with a conventional inflation device. A wide range of configurations and materials may be suitable for use as or in the fluid adjustment member 205 in this embodiment. For example, the fluid adjustment port 210 may include a self-sealing valve that remains closed unless penetrated by a needle or other inflation device.

After implanting the prosthesis 10 illustrated in FIG. 7, a clinician may monitor a patient's condition over time to determine the effectiveness of the prosthesis 10. If the clinician decides to add or remove fluid, the clinician may insert a needle into the fluid adjustment port 210 and add or remove fluid as desired. However, if the clinician determines that the patient would benefit from a urethral prosthesis such as those illustrated in FIGS. 1-3 and 5, the clinician may make an incision in the region of the fluid adjustment member 205, detach the fluid adjustment member 205, and then attach a pressurized restrictor 70 and/or pressurized reservoir 110. After attaching the restrictor 70 and/or pressurized reservoir 110, the prosthesis functions in the same manner as the embodiments illustrated in FIGS. 1-3 and 5.

In one example of this embodiment, the fluid adjustment member 205 is removed by cutting the conduit 50 near the fluid adjustment member 205, and the restrictor 70 and pressurized reservoir 110 are then attached to the conduit 50. It may be necessary to clamp or otherwise restrict fluid flow from the conduit 50 during this procedure.

Alternatively, the prosthesis 10 may be configured with an adapter (not shown) providing for easy detachment of the fluid adjustment member 205 and attachment of the pressurized reservoir 110 and restrictor 70. In this example, the adapter may be configured to prevent fluid from leaking out of the pillow during the attachment and detachment steps. In yet another example, the prosthesis 10 may be configured with a restrictor 70 that is removably attachable to the fluid adjustment member 205 and the pressurized reservoir 110. Because the restrictor 70 generally resists transfer of fluid out of the inflatable pillow 30 unless sufficient pressure is applied, the removal of the fluid adjustment member 205 and the attachment of the pressurized reservoir 110 could be achieved without substantial fluid loss.

We claim:

1. An implantable urethral prosthesis comprising:
    an elongate strip of flexible material including first and second ends and a center point, the first and second ends adapted to be secured to soft tissue in the vicinity of a patient's descending rami;
    an inflatable pillow attached to the center point of the elongate strip that is adapted to exert a force on the patient's urethra when inflated with an inflating agent, the inflatable pillow including a compression region having a tactile locator that is adapted to be contacted to compress the inflatable pillow by exerting pressure on the patient's skin;
    a pressurized reservoir in fluid communication with the inflatable pillow that is adapted to receive inflating agent from, and transfer inflating agent to, the inflatable pillow; and
    a restrictor adapted to regulate the transfer of the inflating agent between the pressurized reservoir and the pillow such that the pressurized reservoir and the pillow are in equilibrium when the pillow is inflated, and wherein upon compression of the inflatable pillow, the inflating agent transfers from the inflatable pillow to the pressurized reservoir.

2. The urethral prosthesis of claim 1 wherein the elongate strip comprises a mesh material.

3. The urethral prosthesis of claim 1 wherein the elongate strip is coated with an elastomer, silicone, polypropylene, polyester, polyurethane, or derivatives or combinations thereof.

4. The urethral prosthesis of claim 1 wherein the elongate strip has a width between about 1.5 and about 2.5 cm.

5. The urethral prosthesis of claim 1 wherein the elongate strip has a length between about 10 and about 15 cm.

6. The urethral prosthesis of claim 1 wherein the inflatable pillow comprises an elastomeric material.

7. The urethral prosthesis of claim 1 wherein the inflatable pillow comprises a silicone material.

8. The urethral prosthesis of claim 1 wherein the inflatable pillow is adapted to have a pressure of between about 50 and about 140 cm $H_2O$ when in equilibrium with the pressurized reservoir.

9. The urethral prosthesis of claim 1 wherein the inflatable pillow is removably attached to the substrate.

10. The urethral prosthesis of claim 1 wherein the pressurized reservoir comprises an elastomeric material.

11. The urethral prosthesis of claim 1 wherein the pressurized reservoir comprises a silicone material.

12. The urethral prosthesis of claim 1 wherein the pressurized reservoir is disposed on the side of the elongate strip opposite the inflatable pillow.

13. The urethral prosthesis of claim 1 wherein the restrictor regulates the transfer of the inflating agent such that after terminating compression, the inflating agent transfers to the inflatable pillow over a sufficient amount of time to allow voiding of a patient's bladder prior to the inflatable pillow and reservoir reaching equilibrium.

14. The urethral prosthesis of claim 1 wherein the restrictor comprises a ball-and-seat valve.

15. The urethral prosthesis of claim 14 wherein the restrictor comprises a fluid resistor.

16. The urethral prosthesis of claim 15 wherein the resistor is a small orifice fluid resistor.

17. The urethral prosthesis of claim 1 wherein the restrictor comprises at least one fluid conduit extending between the pressurized reservoir and the pillow.

18. The urethral prosthesis of claim 17 wherein the conduit comprises a flexible tube having a first end in fluid communication with the inflatable pillow, and a second end in fluid communication with the reservoir.

19. The urethral prosthesis of claim 1 wherein the pressurized reservoir is disposed on the side of the elongate strip opposite the inflatable pillow, and the compression region is contained within the pressurized reservoir.

20. The urethral prosthesis of claim 19 wherein the compression region comprises a stiffener.

21. The urethral prosthesis of claim 20 wherein the stiffener comprises a silicone stiffener.

22. The urethral prosthesis of claim 20 wherein the stiffener comprises a fluid orifice.

23. The urethral prosthesis of claim 1 further comprising a first connector attached to the first end of the elongate strip and a second connector attached to the second end of the elongate strip, wherein the connectors are adapted to removably attach to a guide instrument during implantation.

24. A method of treating urinary incontinence in a patient comprising:
  implanting a urethral prosthesis comprising:
    securing a first side of an elongate strip of a flexible material to soft tissue in the vicinity of the patient's descending rami,
    securing a second side of an elongate strip of a flexible material to soft tissue in the vicinity of the patient's descending rami,
    positioning an inflatable pillow attached at a center point of the elongate strip under the patient's urethra, the inflatable pillow adapted to exert a force on the urethra when inflated with an inflating agent,
    implanting a pressurized reservoir in the patient, the pressurized reservoir in fluid communication with the pillow to receive inflating agent from, and transfer inflating agent to, the inflatable pillow, and
    implanting a restrictor to regulate the transfer of the inflating agent between the pressurized reservoir and the pillow such that the pressurized reservoir and the pillow are in equilibrium when the pillow is inflated, and wherein upon compression of the inflatable pillow, the inflating agent transfers from the inflatable pillow to the pressurized reservoir;
  exerting sufficient pressure on the patient's skin in the vicinity of the inflatable pillow to compress the inflatable pillow and to reduce the force exerted by the inflatable pillow on the portion of the patient's urethra;
  terminating the pressure exerted on the inflatable pillow to allow the inflatable pillow to inflate; and
  voiding the bladder before the inflatable pillow and reservoir reach equilibrium.

25. The method of claim 24 wherein the implanting step comprises positioning the inflatable pillow to contact a portion of the patient's bulbar urethra.

26. The method of claim 24 wherein the implanting step comprises positioning the pressurized reservoir, restrictor or both in a scrotum of a male patient.

27. The method of claim 24 wherein the elongate strip further comprises a connector at each end of the strip, and wherein the implanting step further comprises removably attaching a guide instrument to each of the connectors to implant the elongate strip in the vicinity of the patient's descending rami.

28. The method of claim 24 wherein the elongate strip is positioned anterior to the pubic symphysis.

29. The method of claim 24 wherein the elongate strip is positioned posterior to the pubic symphysis.

30. The method of claim 24 wherein the elongate strip is positioned transobturator relative to the pubic symphysis.

* * * * *